United States Patent [19]

Jacobson

[11] Patent Number: 5,591,218
[45] Date of Patent: Jan. 7, 1997

[54] CURRENT LIMITER FOR IMPLANTABLE ELECTRONIC DEVICE LEAD

[75] Inventor: Peter Jacobson, Haguenau, France

[73] Assignee: ELA Medical, S.A., Montrouge, France

[21] Appl. No.: 287,835

[22] Filed: Aug. 9, 1994

[51] Int. Cl.⁶ ................................................. A61N 1/08
[52] U.S. Cl. .............................................. 607/63; 128/908
[58] Field of Search ........................ 128/908; 607/1, 607/2, 62, 63

[56] References Cited

U.S. PATENT DOCUMENTS

| | | | |
|---|---|---|---|
| 3,518,986 | 7/1970 | Woods et al. | 128/2.1 |
| 3,521,087 | 7/1970 | Lombardi | 307/237 |
| 3,603,811 | 9/1971 | Day et al. | 307/237 |
| 3,605,728 | 9/1971 | Ogle | 128/908 |
| 3,866,932 | 6/1975 | Suessmilch | 128/908 |
| 3,886,932 | 6/1975 | Suessmilch | 128/2.1 R |
| 3,968,802 | 7/1976 | Ballis | 128/419 PG |
| 4,082,097 | 4/1978 | Mann et al. | 128/419 PS |
| 4,102,348 | 7/1978 | Hihara et al. | 128/422 |
| 4,320,763 | 3/1982 | Money | 128/419 PG |
| 4,440,172 | 4/1984 | Langer | 128/419 D |
| 4,722,363 | 2/1988 | Lombardi | 607/62 |
| 4,725,923 | 5/1988 | Winstrom | 128/419 PG |
| 4,744,369 | 5/1988 | Kroll | 128/908 |

FOREIGN PATENT DOCUMENTS

| | | | |
|---|---|---|---|
| 0546666 | 6/1993 | European Pat. Off. | A61N 1/39 |
| 331893 | 8/1976 | Germany | H02H 9/04 |
| 3240280 | 5/1984 | Germany | H02H 9/04 |

*Primary Examiner*—William E. Kamm
*Attorney, Agent, or Firm*—Orrick, Herrington & Sutcliffe

[57] ABSTRACT

The invention protects circuits connected to low energy stimulating (pacing) or detection (sensing) electrodes of an implantable medical device from high energy pulses generated by the device itself or by external devices such as external defibrillators. It also protects cardiac tissue near the low energy electrodes. The invention provides for an automatic and/or foldback-type unidirectional current limiter in each low energy lead. The invention, when applied to an implantable defibrillator/pacemaker, also provides a shock generator presenting pulses to the pacing electrodes only in the direction blocked by the current limiter.

6 Claims, 2 Drawing Sheets

CURRENT LIMITER FOR IMPLANTABLE ELECTRONIC DEVICE LEAD

FIELD OF THE INVENTION

This invention relates to the protection of implantable electronic devices with leads and electrodes used for low energy stimulation (pacing) or detection (sensing) of tissue, against high energy pulses, more particularly to implantable cardiac pacemakers, implantable cardiac defibrillators, and implantable cardiac defibrillator/pacemakers.

BACKGROUND OF THE INVENTION

As used herein a defibrillator refers to any device intended to revert (i.e., to eliminate or stop) a tachyarrhythmia and/or a fibrillation with electrical energy substantially exceeding the pacing energy provided by implantable cardiac pacemakers.

Implantable cardiac pacemakers generally protect against high-energy pulses from an external source by limiting the voltage across any electrode pair. When an external device applies such a high energy pulse to this electrode pair through a low impedance, high currents flow in the electrodes and the limiting device. These high currents may have a detrimental effect on patient tissue in the region of the electrodes.

Money U.S. Pat. No. 4,320,763 refers to a current-limiter device placed in series circuit between a pacemaker and the proximal end of an electrode, to prevent tissue damage adjacent the distal end of the electrode. Money discloses two circuits, one with field-effect transistors (FET) and one with a bipolar transistor, which limit and then hold the current at a fixed value of approximately 20 mA.

Langer U.S. Pat. No. 4,440,172 refers to circuitry intended to protect an ECG sensing amplifier against defibrillation pulses, including a high-value resistor in series with the amplifier input, and clamping diodes across that input, on the proximal side of the resistor. A protected pacing circuit, which couples high frequency energy via an isolating transformer to a demodulator, in turn applies the demodulated pulse to the pacing electrodes. A reverse-biased diode is said to protect this circuitry during defibrillation.

Leinders U.S. Pat. No. 4,595,009 refers to a defibrillator/pacemaker which connects together the pacing and sensing electrodes at the moment it delivers a defibrillating pulse.

Winstrom U.S. Pat. No. 4,745,923 refers to a protection circuit for an implantable device, connected in series with a lead of a pacemaker to protect against high voltages and currents of defibrillators and other sources. The disclosed circuit limits current in either direction in a single lead (the patent shows the circuit in the return, or positive, pacing lead), and uses foldback current limiting, which is frequently used in commercial electronic power supplies (See, Section 6.05, Horowitz and Hill, *The Art of Electronics,* Cambridge University Press, 1989). In a foldback current limiter, impedance remains low until current reaches a first preset limit. Once current exceeds this first limit, impedance remains high until current falls below a second preset limit that is lower than the first preset limit. The Winstrom limiter circuit has a low impedance path between its terminals consisting of a field effect transistor (FET) in series with a low-value resistor. A bipolar transistor opens the FET when the voltage across the low-value resistor exceeds the base-to-emitter threshold of the bipolar transistor (the first preset limit in the foldback current limiter).

Tarjan U.S. Pat. No. 4,787,389 refers to a defibrillator/pacemaker system which opens switches between the pacemaker and its leads during the time it activates its defibrillator.

Bocchi British patent 2,234,908 shows a defibrillator/pacemaker with a protection switch in series with the pacing tip electrode, and a control signal to open the switch during defibrillation and close the switch during pacing.

Pless U.S. Pat. No. 5,111,816 refers to a defibrillator/pacemaker with a single N-channel metal-oxide-semiconductor field-effect transistor (MOSFET) switch in series with each pacing and sensing lead. The device opens these switches when it delivers a shock. When opened, these switches do not allow current to enter the leads from positive voltage sources with respect to pacing ground. The shock generator has its negative power supply referred to pacing ground, so that it only produces positive voltages with respect to pacing ground, thus within the operating range of the protection circuit. In the shock circuit, a diode is in series with each shock delivery switch, to prevent reverse current from flowing in shock circuit switches when external high energy pulses arrive at the shock electrodes. The diodes are said to be added because semiconductor switches withstand high voltage applied with one polarity, but only a few volts applied with opposite polarity. This applies equally to MOSFETs, bipolar junction transistors, and insulated-gate bipolar transistors (IGBTS). Making the switches block current in both directions prevents current from flowing in the shock generator power supply leads during external high energy pulses.

It is apparent that an implantable electronic device, such as a defibrillator/pacemaker must protect its low energy leads, such as pacing and sensing leads, against defibrillation pulses and other high-energy pulses. Although the aforementioned references address this objective, each suffers from one or more deficiencies.

A problem with the Langer patent circuit is that the diode in series with one of the pacing electrodes protects against an external defibrillator only when that defibrillator output pulse happens to fall in a preferred direction upon Langer's circuit, namely the direction where the diode does not conduct. Langer's circuit also requires a transformer, which is difficult to implement with integrated circuit technology.

A problem with the Leinders patent circuit is that it short-circuits the pacing and sensing leads, allowing defibrillation current to flow in their electrodes, with possible adverse effects on patient tissue near these electrodes.

A problem with the Tarjan, Bocchi, and Pless patent circuits is that each opens the pacing and sensing leads, but only in response to a control signal from the implant when it delivers its own high energy pulse. None has any means to detect high energy pulses from external sources and activate the protection circuits automatically.

A problem with the Money patent circuit, which limits the current in the leads to a fixed value, automatically, is that limiting to a fixed value requires a limiting device to dissipate power equal to the product of the limiting current and the applied voltage. Applied power reaches at least 1000 V at 20 mA, or 20 W. The current in such circuits also tends to oscillate about the limiting value, considering the high applied power. These oscillations can adversely affect operation of nearby circuits. Moreover the circuit construction must permit dissipation of this power.

A problem with the Winstrom patent circuit, which provides an automatic foldback current limiter to overcome the oscillation and dissipation concerns of limitation at a constant value, is that the circuit only opens the MOSFET switch in a low-impedance path after first actuating a second bipolar transistor switch, whose delay can result in a high-current spike through the limiter when a defibrillator applies a pulse with fast risetime to the pacing and sensing leads. See Benson U.S. Pat. No. 4,823,796, which describes such an external defibrillator that produces a trapezoidal pulse by transistor discharge of a capacitor with no series inductor. Measurements show such circuits can produce slew rates of thousands of volts per microsecond. Any delay in the protection circuit will result in a current spike, which may couple to and affect nearby circuitry.

Another problem with the Winstrom patent circuit is that it refers only to a bidirectional limiter for use in a single lead. The purpose is to limit current in one lead in a lead pair when a defibrillator applies energy in either polarity. Consequently, in the dual-chamber defibrillator/pacemakers, with two lead pairs, the Winstrom circuit would need to be applied in three of the four leads and results in a relative high part count, i.e., more components than a unidirectional limiter located in each lead.

A problem with the Pless patent circuit is that the shock generator is referenced to ground, which requires positive control voltages for the shock generator and negative control voltages for pacing and sensing. This increases the circuit complexity.

There thus remains a need for improved circuits for protecting low energy pacing and Sensing leads and electrodes from high energy pulses.

SUMMARY OF THE INVENTION

It is, therefore, an object of the present invention to improve the protection of low energy pacing and sensing leads (also called "low energy leads") of electronic medical devices from high energy pulses.

Broadly, the present invention pertains to protecting the circuitry connected to the low energy leads, and protecting the patient's tissue at the low energy lead sites, from the high energy pulses delivered by the implanted device, and from high energy pulses from other medical electronic devices, such as external defibrillators. The invention also applies to any electronic devices which require protection against high energy pulses.

One aspect of the invention is directed to apparatus for protecting against external high energy pulses of either polarity. One such apparatus includes a circuit which operates to limit the current through the pacing and sensing leads, instead of limiting the voltage across them, to protect cardiac tissue in the region of the cardiac electrode terminals of the pacing and sensing leads, i.e., the electrodes in direct contact with or in close proximity to cardiac tissue (also called direct cardiac electrodes).

The current limiting circuit is automatically activated, to protect against external high energy pulses, as well as high energy pulses delivered by the implanted the device. Foldback current limiting is preferably used to reduce power dissipation and eliminate oscillation in the limiter. The foldback current limiter is preferably activated with a single transistor switch, to provide rapid response to fast risetime external defibrillation pulses.

In application to an implantable defibrillator/pacemaker, the invention also concerns referring the shock generator to a negative supply with respect to pacing ground. This advantageously permits the use of negative control voltages for both shock and pacing and hence, simplifies the circuit for operation of these functions.

In a preferred embodiment, the present invention provides one automatic unidirectional foldback current limiter in each pacing and sensing lead, which limits currents entering the leads. In the presence of an external high-energy pulse, only limited current can enter every pacing and sensing electrode, thus only limited current can flow in any pacing and sensing electrode.

Each automatic foldback current limiter rapidly limits current to a first value with a single transistor switch, and then somewhat later entirely opens this first switch with a second switch to prevent oscillations, until the current falls below a second lower value.

According to a further aspect of the invention, when applied to a defibrillator/pacemaker, the shock generator circuit provides positive pulses with respect to a low-voltage negative supply. In addition, diodes are placed in series with the shock generator switches to prevent current from flowing in the shock generator circuit during external high-energy pulses applied to the shock electrodes. Internal high energy pulses, which the shock generator makes positive with respect to the low-voltage negative supply, can only enter the pacing leads with limited current, as soon as the magnitude of their voltage exceeds the magnitude of the low voltage supply. Since external high energy pulses cannot cause current to flow in the shock electrodes or power supply, then they can only cause current to flow in the pacing and sensing electrodes, which is limited in accordance with the invention as explained above.

Another aspect of the present invention is directed to an implanted medical device for low energy pacing and detection of tissue having electrodes in contact with the tissue, a control circuit to control the low energy pacing and sensing, and leads connecting the electrodes to the control circuit, an apparatus for protecting the control circuit and the tissue adjacent the electrodes, in which the improvement comprises an automatic, unidirectional current limiting circuit in series with each low energy lead, the current limiting circuit having an unprotected input to the tissue and a protected output to the control circuitry.

In accordance with this aspect of the invention, each current limiting circuit is a foldback current limiter. Further, each current limiting circuit preferably includes: a source, having a bias voltage; a limiting device having a voltage drop from the input to the output, a first state for not limiting the current between the input and output, a second state for limiting the current between the input and output to a first preset value, the limiting device being responsive to the bias voltage and automatically changing from the first state to the second state, and a third state having an open circuit condition; and a switch means having an inactive state and an active state, the active state placing the limiting device in the third state in response to the limiting device automatically changing from the first state to the second state and the voltage drop across the limiting device input and output exceeding a preset value.

The limiting device preferably includes: a field effect transistor (FET) having a source, drain and gate, the drain being connected to the unprotected input, the FET drain to source current path being closed in the first and second states and open in the third state; a current sensing means connecting the FET source to the unprotected output; and a bias means for connecting the bias voltage to the FET gate wherein, the FET gate to source voltage is above the FET threshold voltage when the FET is closed. The current sensing means may be a low value resistor, for example, on the order of 39 ohms.

The switch means preferably includes: means for monitoring the voltage drop across the limiting device input and output; means for changing the switch means from the inactive state to the active state when the sensed voltage drop exceeds a preset limit; and means for placing the limiting device in the third state condition when the switch means is in the active state.

The monitoring means is preferably a resistive voltage divider connected to the limiting device. The switch and the changing means are preferably a bipolar transistor having a base, emitter, and collector, in which the transistor base is connected to the monitoring means, the collector is connected to the bias voltage, and the emitter is connected to the protected output. The placing means preferably operates by effectively lowering the bias voltage applied to the limiting device. A high impedance bias source of, for example, several megohms is preferably employed to reduce power dissipation when it is short circuited with the bipolar transistor.

The implanted medical device is preferably a cardiac control device, such as a pacemaker. The medical device also may include a shock generator able to deliver a shock current to the tissue, in which the shock current arriving at the low energy leads is polarity blocked and limited by said unidirectional current limiting circuits having the corresponding polarity. The medical device preferably has a pacing ground potential and the shock generator is characterized by a shock power supply having a supply voltage connected to a reference voltage that is near said pacing ground potential. The reference voltage is preferably a negative value, and the shock power supply voltage is positive with respect to the reference voltage. The shock generator preferably includes a pair of leads for use in delivering a shock current to the tissue, a plurality of switches for selectively connecting the shock power supply voltage to the reference voltage, and means, such as a programmed control circuit, for controlling said switches to deliver a shock current from one shock lead to the other with a selected polarity, and a diode structure in series with each shock switch for rendering said shock switch bidirectionally blocking.

In a preferred embodiment, the current limiting devices and the shock generator are constructed as a monolithic integrated circuit. Alternately, commercial discrete transistors and other components could be mounted on a common ceramic substrate to form a hybrid micro-circuit, e.g., using thin film and/or thick film technologies.

The invention also is directed to a circuit for limiting the current flowing in one direction from an unprotected input to a protected output, for use in series with the lead of an implanted medical device having low energy tissue sensing and/or tissue stimulation electrodes, including but not limited to cardiac monitoring and/or control devices. One such circuit includes:

a source having a bias voltage;

a first switch having an open circuit condition, and a closed circuit condition including a low current limiting condition, the first switch having an input connected to the unprotected input and an output;

a low value resistor connected to the output of the first switch having a voltage in response to current flow through the first switch;

a second switch having an open circuit condition and a closed circuit condition;

a clamp circuit to maintain the protected output voltage within a preset voltage range of a ground potential; and a voltage divider connected to the unprotected input and the protected output and producing a control voltage corresponding to the voltage across the unprotected input and the protected output.

The first switch is biased in the closed circuit condition when the voltage of the low value resistor is below the bias voltage by a predetermined amount. When the voltage of the low value resistor is not below the bias voltage by the first predetermined amount, the first switch automatically changes to a constant low current limiting state, wherein the first switch and the resistor act together to limit the current through both at $I=(V_b-V_t)+R$; where $V_b$ is the bias voltage, $V_t$ is the threshold voltage of the first switch, and R is the value of the resistor. The second switch automatically changes between the open circuit condition, when the control voltage is less than a second predetermined amount, and the closed circuit condition when the control voltage is greater than the second predetermined amount. The second switch changing to the closed circuit condition effectively lowers the bias voltage to place and maintain the first switch in the open circuit condition.

The first switch is preferably an N channel enhancement FET having a gate connected to the bias voltage, a drain connected to the unprotected input, and a source connected to the low value resistor, and the first predetermined voltage is the FET threshold voltage. The second switch is preferably a bipolar transistor having a collector connected to the bias voltage, an emitter connected to the protected output, and a base connected to the control voltage of the voltage divider, and the second predetermined voltage is the base to emitter threshold voltage of the transistor. The voltage divider includes a first resistor connected between the unprotected input and the transistor base and a second resistor connected between the transistor base and the protected output. A zener diode is preferably connected between the transistor collector and emitter to protect the FET against breakdown due to very fast risetime pulses coupled to the FET gate-source capacitance by its drain-source capacitance.

Preferably, the implanted medical device is a pacemaker having a plurality of leads connected to cardiac tissue, wherein one unidirectional current limiting circuit is interposed in series with each lead with its protected output connected to the pacemaker. However, the invention is equally applicable to other medical devices which sense tissue and/or stimulate tissue at low energy levels.

Another aspect of the invention concerns an apparatus for a generating shock current for application to tissue. One such apparatus includes:

a source of high voltage having a positive terminal and a negative terminal;

a source of bias voltage connected to the negative terminal of the high voltage source;

a first and a second switch connected together at a first junction and in series between the positive and negative terminals of the high voltage source;

a third and a fourth switch connected together at a second junction and in series between the positive and negative terminals of the high voltage source, each of the first, second, third and fourth switches having an open circuit and closed circuit condition;

a first shock lead connected to the first junction and a second shock lead connected to the second junction;

means for controlling the first, second, third and fourth switches for delivering a shock current from the positive terminal of the high voltage source through the first and second shock leads to the negative terminal of the high voltage source, said shock current having a first polarity through the first and second shock leads when the first and fourth switches are closed and the second and third switches are open, and the reverse polarity when the third and second switches are closed and the first and fourth switches are open; and a plurality of diodes such that at least one diode is connected between each of the first switch and the high voltage source, the third switch and the high voltage source, the second switch and the first shock lead, and the fourth switch and the second shock lead, thereby rendering the shock generator bidirectionally blocking. Alternately, the high side diodes could be respectively connected between the first switch and the first shock lead and between the second switch and the second shock lead.

In a preferred embodiment of this aspect of the invention, the construction of the shock generator is a monolithic integrated circuit structure. Each of the first, second, third and fourth switches includes an insulated gate bipolar transistor (IGBT) having a base, collector and emitter, with the collector on the high voltage side of the transistor and the plurality of diodes respectively connected to the transistors with the diode cathode connected to the transistor collector. Each of the IGBTs and diodes have a high breakdown voltage, preferably on the order of 1000 volts. Alternately, commercial discrete transistors and other components could be mounted on a common ceramic substrate to form a hybrid micro-circuit.

BRIEF DESCRIPTION OF THE DRAWINGS

Further features of the invention, its nature and various advantages will become apparent from the accompanying drawings and the following detailed description of the invention, in which like reference characters refer to like elements, and in which.

DETAILED DESCRIPTION OF THE INVENTION

Figure 1:
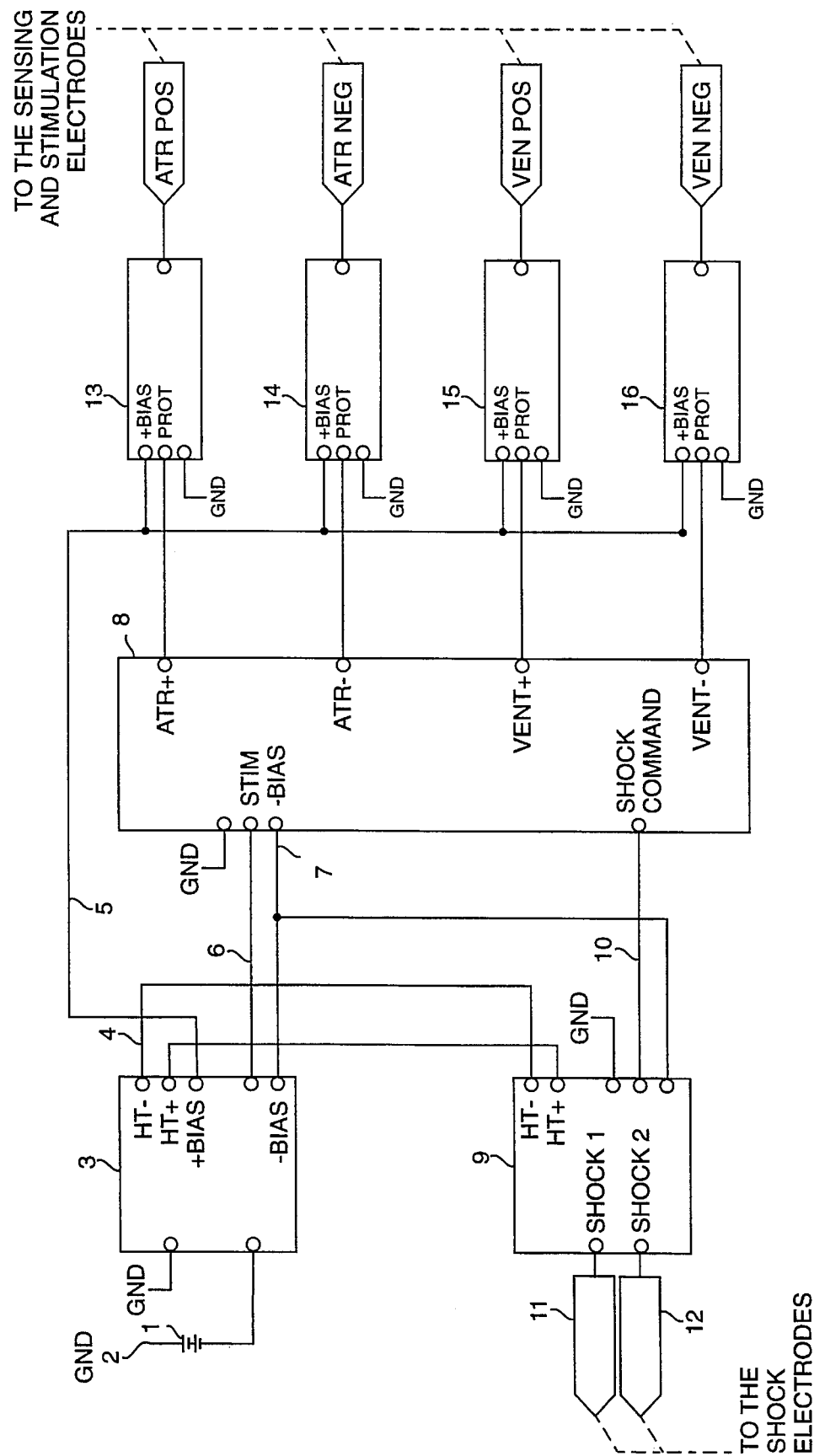
FIG. 1 shows a schematic block diagram of an apparatus in accordance with an embodiment of the invention, applied to an implantable defibrillator/pacemaker.

FIG. 1 shows an overview of the invention applied to an implantable defibrillator/pacemaker with atrial and ventricular pacing and sensing, and with multiphasic shock. The device includes a battery 1, a power supply 3, low voltage circuits 8, a shock circuit 9, and current limiters 13, 14, 15 and 16. Battery 1 powers the device. Ground 2 serves as reference voltage (0 Volts) for all device signals, unless otherwise noted. Power supply 3 converts the voltage of battery 1 to other supply voltages to power the device. These other voltages include:

(i) high voltage supply 4 having positive terminal HT+ and negative terminal HT−, for a shock generator 9, at approximately 0.75 KV, the negative supply HT− being connected to a −Bias supply 7, not to ground 2;

(ii) +Bias supply 5, for the current limiters 13–16, at approximately 9.0 V;

(iii) Pacing voltage supply 6, at approximately −6.0 V; and (iv) −Bias supply 7, for low voltage circuits 8 and the shock generator 9, at approximately −9.0 V.

Referring to FIG. 1, low voltage circuits 8 provide pacing, sensing and control. They operate between ground 2 and −Bias supply 7. Because the value of pacing voltage supply 6 is between these two supply voltages, low voltage circuits 8 can advantageously generate and measure pacing and sensing signals directly, without any level-shifting. When low voltage circuits 8 sense atrial and/or ventricular signals requiring shock, they signal shock generator 9 via a shock control bus 10.

Shock generator 9 provides high voltage shocks between a pair of shock leads 11 and 12, when low voltage circuits 8 trigger it via shock control bus 10. Shock energy comes from high voltage supply 4 referred to −Bias supply 7.

Limiters 13, 14, 15, and 16 protect low voltage circuits 8, and the tissue adjacent to the pacing and sensing electrodes (not shown) connected to leads 17, 18, 19, and 20, from shocks delivered by shock generator 9 or by an external defibrillator (not shown).

Figure 2:
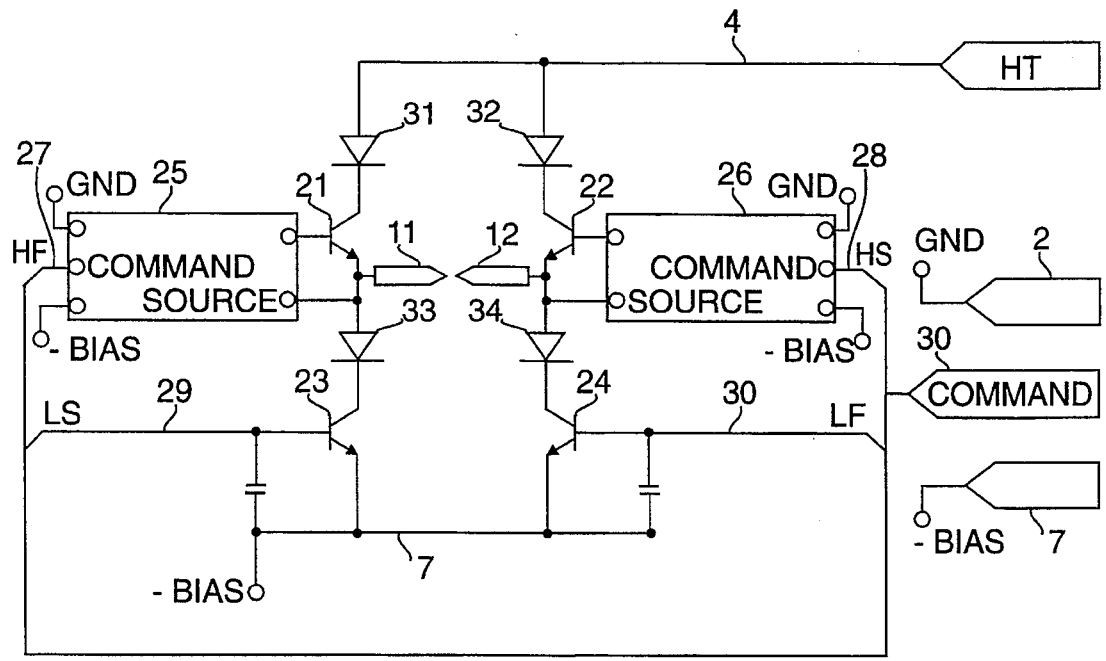
FIG. 2 shows a schematic diagram of the shock generator.

Referring to FIG. 2, shock generator 9 operates four switches 21, 22, 23, 24, which are configured in an "H bridge", commonly used to drive an alternating current through a load from a direct current supply. Switches 21–24 are preferably insulated gate bipolar transistors (IGBT). IGBTs are used because they have output characteristics like NPN bipolar transistors but can be driven like N-channel enhancement MOSFETs.

Isolators 25 and 26 turn on (close) the high side switches 21 and 22 in response to control signals HF at lead 27 and HS at lead 28, respectively. Control signals LS at lead 29 and LF at lead 30 turn on (close) the low side switches 23 and 24 respectively. Since the sources of switches 23 and 24 connect to −Bias supply 7, control signals LF and LS operate from −Bias supply 7 to ground 2, with no voltage translator (level-shifting). The circuit only requires isolators 25 and 26 for the high side switches 21 and 22, because the sources of switches 21 and 22 reach high voltage during shock.

The circuit in FIG. 2 generates a monophasic or multiphasic shock. When the low voltage circuits 8 assert control signals HF at lead 27 and LF at lead 30, this turns on switches 21 and 24, and current flows from the high voltage supply 4, through switch 21, out the Shock-1 lead 11, in the Shock-2 lead 12, through switch 24, and returns to the −Bias supply 7. As explained above, power supply 3 produces high voltage supply 4 referenced to −Bias supply 7. Alternatively when low voltage circuits 8 assert signals HS at lead 28 and LS at lead 29, the circuit provides current in the opposite direction between the same shock leads 11 and 12.

Diodes 31, 32, 33, and 34 prevent reverse current from flowing in switches 21 through 24 during application of a voltage pulse from an external source to the shock leads 11 and 12. The external pulse voltage must exceed the sum of the diode and transistor breakdown voltages for current to flow between shock electrodes 11 and 12, and it must exceed either the diode or transistor breakdown voltage for current to flow at all (e.g., to ground 2 or to −Bias supply 7).

Since the circuit shown in FIG. 2 references shock generator 9 to −Bias supply 7, the voltage at either shock electrode 11 or 12, during a shock generated by the device, must fall in the range from the −Bias supply 7 voltage to the high voltage supply 4. Moreover, any external shock not exceeding the breakdown voltage of the diode or transistor in the circuit will not cause current to flow through either shock lead 11 or 12, and thus will not cause current to flow in any of the power supplies: ground 2, −Bias 7, or high voltage 4.

Figure 3:
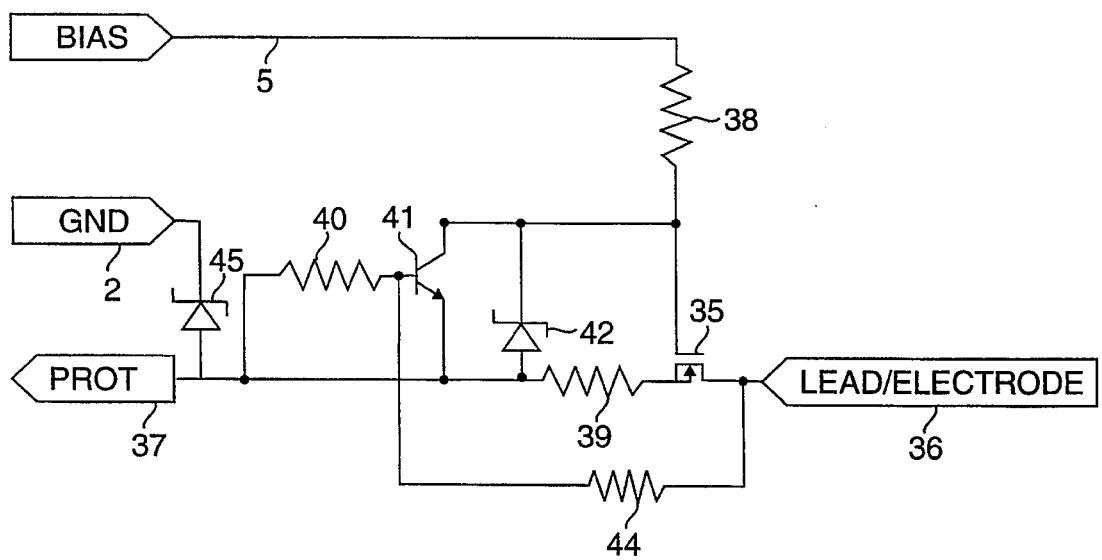
FIG. 3 shows a schematic diagram of the unidirectional foldback current limiter of FIG. 1.

Referring now to FIGS. 1 and 3, each of limiter circuits 13–16 includes a high-voltage transistor switch 35, preferably an N-channel MOSFET. Such transistors exist commercially in small die sizes with thresholds of approximately 5 Volts and on-resistances typically less than 10 Ohms at a gate-source voltage of 9 Volts; for example, commercial models IRFBG20 or BUK456/1000B.

In FIG. 3, the voltages on the lead terminal 36 and the lead terminal 37 of the limiter, in normal operation in the absence of internal or external high-energy pulses, range between the −Bias supply 7 and a few hundred millivolts above ground 2.

While the voltages in lead terminals 36 and 37 remain in this normal operating range, the +Bias voltage supply 4 holds transistor 35 on, via a resistor 38. Since transistor 35 draws no gate current, except leakage current, the +Bias supply 4 has a low current requirement. Since the power supply 3 must generate the +Bias supply 4 by inverting the battery voltage, this low current requirement permits using a small capacitive inverter with few components, and advantageously can be formed as an integrated circuit. If the architecture of the invention instead placed the battery above ground and inverted the battery voltage to provide pacing, this would require much higher current capacity in the inverter (especially for rapid pacing for arrhythmia reversion), eliminating the possibility of integration.

The circuit shown in FIG. 3 includes a low-value resistor 39 in series with the source of transistor 35. Resistor 39 together with transistor 35 provide a low-impedance path between lead 36 and protected lead terminal 37, when transistor 35 conducts in its normal state. Let $V_b$ equal the bias voltage 5, $V_t$ equal the threshold of transistor 35 and R equal the resistance of resistor 39. If the current through resistor 39 increases so that the voltage across resistor 39 reaches $V_b - V_t$, this limits the current through transistor 35 to $(V_b - V_t)/R$, typically 0.15 A.

When transistor 35 limits current in this manner, voltage at lead terminal 36 rises until the base-emitter voltage of transistor 41, set by a voltage divider consisting of resistors 44 and 40, exceeds the threshold of that transistor 41. This turns on transistor 41, clamping the gate-source voltage of transistor 35 to zero. This turns transistor 35 off and it no longer dissipates power. It is then in an open circuit condition. As a result, the current flows through the high impedance elements 44 and 40 between lead terminals 36 and 37. The circuit remains in this high-impedance state until the voltage across its terminals falls to a point where transistor 41 turns off, allowing resistor 38 to turn transistor 35 back on, restoring the low impedance path through transistor 35 and resistor 39.

Zener diodes 42 and 43, shown in FIG. 3, protect the gate-source junction of transistor 35, and the low voltage circuitry 8 illustrated in FIG. 1, respectively. Zener diode 43 also provides a circuit for clamping the voltage at the protected output within a fixed voltage range of the ground potential, which enables the current and voltage limiting functions of the unidirectional current limiting circuit.

Although the invention has been described with reference to a particular embodiment, it is to be understood that this embodiment is merely illustrative of the application of the principles of the invention. Numerous other modifications may be made and other arrangements may be devised without departing from the spirit and scope of the present invention.

I claim:

1. A unidirectional current limiting circuit for use in series with the lead of an implanted medical device having low energy stimulation and detection electrodes, comprising:

an unprotected input and a protected output;

a current flow from the unprotected input to the protected output;

a reference potential corresponding to a ground potential;.

a bias voltage;

a first switch having an open circuit condition, a current limiting condition, and a closed circuit condition, the first switch having an input connected to the unprotected input and an output;

a low value resistor connected to the output of the first switch producing a first voltage in response to said current flow through the first switch;

a second switch having an open circuit condition and a closed circuit condition the second switch being operatively connected between the bias voltage and the protected output;

a voltage divider connected to the unprotected input and the protected output, said voltage provider and producing a control voltage corresponding to a voltage across the unprotected input and the protected output; and a voltage clamp circuit connected between the reference potential and the protected output and operable to maintain the protected output voltage within a preset voltage range of the reference voltage;

wherein the first switch is biased in the closed circuit condition when the voltage of the low value resistor is below the bias voltage by a first predetermined amount, the first switch is biased in the current limiting condition when the voltage of the low value resistor is not below the bias voltage by the first predetermined amount, and wherein the second switch is automatically biased in the open circuit condition when the control voltage is less than a second predetermined amount and in the closed circuit condition when the control voltage is greater than the second predetermined amount, the second switch closed circuit condition effectively lowering the bias voltage to place and maintain the first switch in the open circuit condition.

2. The apparatus of claim 1 wherein the first switch further comprises an N channel enhancement FET having a gate connected to the bias voltage, a drain connected to the unprotected input, and a source connected to the low value resistor, and the first predetermined amount is the FET threshold voltage.

3. The apparatus of claims 1 wherein the second switch is characterized by an NPN bipolar transistor having a collector connected to the bias voltage, an emitter connected to the protected output, and a base connected to the control voltage of the voltage divider, and the second predetermined amount is the base to emitter threshold voltage of the transistor.

4. The apparatus of claim 3 wherein the voltage divider further comprises a first resistor connected between the unprotected input and the transistor base and a second resistor connected between the transistor base and the protected output.

5. The apparatus of claim 1 further comprising a zener diode connected between the transistor collector and emitter.

6. The apparatus of claim 1 wherein the voltage clamp circuit further comprises a zener diode.

* * * * *